United States Patent [19]

Scheefers

[11] Patent Number: 4,716,122

[45] Date of Patent: Dec. 29, 1987

[54] CARRIER MATERIAL FOR USE IN IMMUNE DETERMINATIONS

[75] Inventor: Hans Scheefers, Giessen, Fed. Rep. of Germany

[73] Assignee: Organogen Medizinisch-Molekularbiologische Forschungsgesellschaft m.b.H., Heidelberg, Fed. Rep. of Germany

[21] Appl. No.: 780,378

[22] Filed: Sep. 26, 1985

[30] Foreign Application Priority Data

Sep. 28, 1984 [DE] Fed. Rep. of Germany ....... 3435744

[51] Int. Cl.⁴ ................. G01N 33/543; G01N 33/544; G01N 33/545; G01N 33/549
[52] U.S. Cl. .................................... 436/532; 436/518; 436/528; 436/531; 436/828; 436/905
[58] Field of Search ............... 436/518, 532, 828, 905, 436/528, 531; 260/349; 548/542, 545, 548, 473; 526/352

[56] References Cited

U.S. PATENT DOCUMENTS

| 3,896,217 | 7/1975 | Johnson | 436/808 X |
| 3,995,018 | 11/1976 | Sjöquist | 436/823 X |
| 4,046,723 | 9/1977 | Dorman . | |
| 4,478,946 | 10/1984 | Van der Merwe et al. | 436/524 X |
| 4,608,246 | 8/1986 | Bayer et al. | 435/23 X |

OTHER PUBLICATIONS

European Journal of Biochemistry, Band 73, 1977, J. Sjodahl, "Repetitive Sequences in Protein A from Staphylococcus aureus 2", Seiten 343-351.

Primary Examiner—David M. Naff
Assistant Examiner—Jack Spiegel
Attorney, Agent, or Firm—Felfe & Lynch

[57] ABSTRACT

The present invention provides a carrier such as polyethylene having covalently bound to it a reaction component such as an antibody, for use for immune determinations. The reaction component is covalently bound via heterobifunctional photoactivatable compounds, one group of which is found by an aryl azide group. Protein A may be bound covalently to the carrier via heterobifunctional photoactivatable compounds, and antibodies bound to the protein A.

9 Claims, No Drawings

CARRIER MATERIAL FOR USE IN IMMUNE DETERMINATIONS

The present invention is concerned with a carrier material for use in immune determinations, in which a reaction component of an immunological reaction is covalently bound to the carrier material, and is also concerned with a process for immune determination.

Processes for immune determinations are widely used. The ELISA process is frequently used in which one reaction component of an immune reaction is present adsorbed on to a solid phase. In practice, as solid phase there are thereby preferably used synthetic resin test tubes or microtitre plates which carry a component of the reaction adsorbed on the inner surface. It is also conventional to use spheroids which carry a component of the reaction adsorbed on their outer surfaces.

The most common three processes for enzyme immune determinations are the sandwich process, the indirect process and the competition process.

In the case of the sandwich process, an antibody is adsorbed on the carrier, the test solution is added and the specific antigen contained in the test solution is bound on the antibody. An anzyme-marked specific antibody for the antigen-antibody complex is then added thereto which binds to the complex. Finally, the substrate specific for the enzyme is added, this substrate reacting in a specific manner. The reaction can be evaluated, for example photometrically by measurement of the light absorption or of the optical density, the amount of antigen can be calculated which is directly proportional to the absorption or density.

In the case of the indirect process, an antigen is adsorbed on the carrier material. Test solution is added thereto, the antibody contained in the test solution which is specific for the adsorbed antigen thereby reacting with the antigen. In the case of adding enzyme-marked antiglobulin, the antiglobulin binds to the antigen-antibody complex. After addition of a substrate which is specific for the enzyme, a colour is again formed which can be evaluated by photometric measurement and is directly proportional to the amount of the unknown antibody in the test serum.

In the case of the third process, i.e. the competition process, one of the two components of the immune reaction is adsorbed on the carrier material. A solution is added thereto which contains not only the unknown other component of the immune reaction but also a known amount of enzyme-marked other component of the immune reaction. Both componency now bind competitively with the component of the immune reaction which is adsorbed on the carrier. In the case of a second sample, a standard solution is added which only contains marked component. The enzyme substrate is then added to both solutions and the colour formation is determined by photometric measurement. The difference between standard and sample permit a calculation of the amount of unknown reaction component.

Radio-immune determinations (RIA) are frequently also carried out. The RIA is used as a test for the detection and quantitative determination of antigens and antibodies by radioactive marking of one of the two reaction components. It can be carried out as a solid phase test in which one of the two reaction components is bound to a solid phase, the separation of the antigen-antibody complex from the free component thereby being substantially simplified. The test is carried out using the principle of competitive inhibition. The binding of a radioactively-marked antigen by the specific antibody is thereby inhibited by an unmarked antigen, dependent upon the concentration. The greater is the proportion of the unmarked antigen to be measured, the smaller is the radioactivity of the antigen-antibody complex. In the case of the solid phase RIA, the direct binding test is also possible.

In the case of all of these processes, the carrier material and the component of the immune reaction adsorbed thereon can only be used once for the test, whereafter both are discarded since the bound reaction component of the immune reaction is bound to the carrier material via strong and weak exchange actions, secondary, non-covalent lipophilic, dipole-dipole or ion-dipole interactions. All these bindings do not withstand the drastic conditions which, in the case of a regeneration, lead to a dissociation of the antigen-antibody binding. A certain amount of the component of the immune reaction bound to the carrier material dissolves off in the case of the regeneration process so that a repeated use of the hitherto known carriers is not possible.

From Ann. Rev. Biochem., 35 (I), 879/1966, it is already known to bind proteins via bifunctional reagents to carrier materials. It is also known from Federal Republic of Germany Patent Specification No. 25 23 207 to bind biopolymers via carriers. However, it is not stated how such a covalent binding is to be carriet out. From Angewandte Chemie, 84 (8), 319–330/1972, it is known to carry out the covalent binding via functional groups which are present on the carrier material. Thus, for this purpose, the carrier used must have reactive groups which can covalently bind the reactants via the bridge builders.

Therefore, it was desirable to find a possibility by means of which a protein or a component of an immunological reaction can be covalently bound to the carrier without first having to carry out a derivatisation.

Therefore, it was desirable to find a reuseable carrier material for immune determinations in the case of which a reaction component is so bound to the carrier material that it is not removed in the case of a regeneration reaction.

Thus, it is an object of the present invention to provide a carrier material which contains a bound component of an immune reaction and which can be reused several times.

Thus, according to the present invention, there is provided a carrier material for immune determinations in which one reaction component of the immunological reaction is covalently bound to the carrier material, wherein the reaction component is covalently bound via a heterobi-functional photoactivatable compound, one group of which is formed by an aryl azide group.

As bridge builders, according to the present invention there are preferably used the following compounds: N-5-azido-2-nitrobenzoyloxysuccinimide (ANB-NOS), p-azidophenacyl bromide, p-azidophenylglyoxal, 4-fluoro-3-nitrophenyl azide, methyl 4-azidobenzoimidate hydrochloride, N-succinimidyl-(4-azidophenyldithio)-propionate, N-(4-azidophenylthio)-phthalimide, N-hydroxysuccinimidyl-4-azidobenzoate, N-hydroxysuccinimidyl-4-azidosalicylic acid, N-succinimidyl-6-(4'-azido-2'-nitrophenylamino)-hexanoate, sulphosuccinimidyl 6-(4-azido-2'-nitropheynlamino)-hexanoate, ethyl 4-azidophenyl-1,4-dithioutyrimidate hydrochloride, N-succinimidyl (4-azidophenyldithio)- propionate, sulphosuccinimidyl (4-azidophenyldithio)-propionate, 4,4'-dithio-bis-phenylazide.

The especially preferred compound is Lohmant's Reagent II, i.e. N-succinimidyl 6-(4'-azido-2'-nitrophenylamino)-hexanoate.

As carrier materials, there are usually employed spherpids, microtitre plates or test tubes. These carrier materials consist of a synthetic resin which has the property of adsorptively binding as little reaction component as possible. Furthermore, it must be suitable for binding with the heterobifunctional compound used as bridge builder. Surface-treated polyethylene has thereby proved to be especially suitable, such as is obtainable, for example, under the designation "Minisorp-material" in the form of test tubes from the Danish firm NUNC. It is also possible to use synthetic resin material which, by derivatisation, is suitable for binding with the heterobifunctional compound.

The carrier material according to the present invention is suitable for all kinds of immune determinations and especially for ELISA and solid-phase RIA.

All reaction components of an immunological reaction can be bound to the carrier material. Thus, for example, an antigen, an allergen or an antibody can be covalently fixed to the carrier.

The reaction component is bound to the carrier material via heterobifunctional photoactivatable compounds, one bifunctional group of which is formed by an aryl azide group. Preferred bridge builders are those set out above, Lohmant's reagent, i.e. the known compound N-succinimidyl-6-(4'-azido-2'-nitrophenylamino)-hexanoate, being especially preferred, one side of which carries an aryl azide group which, in a photolysis reaction, initiated by visible light, can be reacted with the formation of a nitrene. The nitrene formed by the photolysis is extremely reactive. It enters non-selectively with regard to its reaction component into a covalent bond with its immediate neighbour. This nitrene generated by the action of light can also react with a relatively inert material and, in the case of the reaction, is not limited to reactive groups of a particular material to be used for special reasons. It even reacts with the chemically relatively inert polyethylene. The other functional group of the preferred bridge builder is an N-hydroxysuccinimide ester which, at an alkaline pH, reacts very gently with non-protonised free amino groups of a reactant, for example a protein. In this way, it is possible to bind, for example, antigens, allergens and antibodies.

According to a further embodiment of the present invention, via the bridgebuilder, protein A (agglutinogen from *Staphylococcus aureus* with four binding points for the Fc region of immunoglobulin G; see J. Sjödahl, Eur. J. Biochem., 73, 343-351/1977) is covalently bound to the carrier material. Added antibodies can then bind with their constant part to the carrier material covalently coated with protein A and the variable parts of the antibodies are then available for the binding of the other component of the immunological reaction. The loading of the carrier so directed increases the biological efficiency of the coating extremely and makes the system, referred to the useable carrier surface, more sensitive. There is then also the possibility to use the carrier covalently coated with the protein A for a further chemical reaction. In the case of this chemical reaction, with the use of a protein A bridge builder, the previously directed antibody adsorptively bound to the protein A can be covalently cross-linked with this so that, after the cross-linking reaction, the antibody is present directed and covalently bound to the carrier.

The reaction component bound via the bridge builder has a certain distance from the carrier material and also a certain mobility. This has a very favourable effect on the accessibility of the covalently bound reaction component which also, in turn, leads to an improvement of the immune reaction.

The carrier material according to the present invention, which carries one component of an immune reaction covalently bound via a bridge builder, can frequently be reused since the reaction component, even under the drastic conditions which are necessary for the regeneration, is not removed from the carrier material since it is presently covalently bound and not adsorptively bound.

The process according to the present invention for the immune determination, in which one of the components participating in the immune reaction is covalently bound to the carrier material, is characterised in that the binding takes place via a heterobifunctional, photoactivatable compound, one group of which is formed by an aryl azide group and preferably via N-succinimidyl 6-(4'-azido-2'-nitrophenylamino)-hexanoate, as bridge builder, the immune determination is carried out and the carrier material, with the component bound thereon, is recovered after the immune reaction.

This process can be repeated as often as desired with the carrier material according to the present invention since the covalently bound component is not removed, even under the drastic reaction conditions of the regeneration but remains attached.

In a further embodiment of the process according to the present invention, protein A is covalently bound to the carrier which then carries an antibody. In this way, the constant parts of the antibody are bound and the variable parts of the antibody are available for the immunological reaction. After carrying out the immunological reaction, the carrier with the covalently bound protein A and the antibody adsorptively or covalently bound thereon can be recovered by regeneration.

The carrier material and the process for immune determination according to the present invention have several advantages. One and the same carrier material can be used very frequently for immune determinations after appropriate regeneration steps. The reuseable carrier material according to the present invention is especially advantageous for immune determinations in which, as reaction component to be bound, a component is used which is only present in a limited amount because it is difficult to prepare or is difficult to isolate or synthesize. In these cases, the amount of reaction component available can be coupled to derivatised carrier material and, in this way, it is possible to carry out substantially more immune determinations with a limited amount of reaction component present. Furthermore, the costs for an individual determination are considerably reduced.

The following Example is given for the purpose of illustrating the present invention:

EXAMPLE

Protein A was bound to a carrier material with the use of N-succinimidyl 6-(4'-azido-2'-nitrophenylamino)-hexanoate (Lohmant's reagent) as bridge building compound. After appropriate washing steps, the carrier bound protein A was allowed to react with the Lohmant's reagent at an alkaline pH with the exclusion of light. Under these conditions, this second bridge builder reacts with the N-hydroxysuccinimide ester as functional group covalently with the carrier bound protein A. After further washing steps, the derivatised carrier-bound protein A was incubated with antibodies which were hereby bound with their constant part to the protein A. After renewed further washing steps, by means of a photochemical reaction, antibodies directed to the protein A could be covalently bound, the variable part of the antibody facing away from the carrier surface and facing towards the antigen to be bound. The so derivatised carrier had a higher loading density and, resulting therefrom, a high enzymatic activity per unit surface area. It could be used for 100 determinations.

We claim:

1. A carrier having a covalently bound reaction component of an immunological reaction, for use in immune determinations comprising the reaction component covalently bound to a heterobifunctional photoactivatable compound, one group of which is formed by an aryl azide group linked to an inert polyethylene carrier.

2. The carrier according to claim 1, wherein the heterobifunctional photoactivatable compound is N-5-azidonitrobenzoyloxysuccinimide, p-azidophenacyl bromide, p-azidophenylglyoxal, 4-fluoro-3-nitrophenyl azide, methyl 4-azidobenzoimidate hydrochloride, N-succinimidyl (4-azidophenyldithio)-propionate, N-(4-azidophenylthio)-phthalimide, N-hydroxysuccinimidyl 4-azidobenzoate, N-hydroxysuccinimidyl 4-azidosalicylic acid, sulphosuccinimidyl 6-(4'-azido-2'-nitrophenylamino)-hexanoate, ethyl 4-azidophenyl-1,4-dithiobutyrimidate hydrochloride, N-succinimidyl (4-azidophenyldithio)-propionate, sulphosuccinimidyl (4-azidophenyldithio)-propionate or 4,4'-dithio-bis-phenylazide, or a combination thereof.

3. The carrier according to claim 1, wherein the heterobifunctional photoactivatable compound is N-succinimidyl 6-(4'-azido-2'-nitrophenylamino)-hexanoate.

4. The carrier according to claim 2, wherein said reaction component is a protein A-antibody complex.

5. In a process for immune determination in which one of the components participating in the immune reaction is covalently bound to a carrier material, wherein the improvement comprises binding said component via a heterobifunctional photoactivatable compound to an inert polyethylene carrier, wherein one group of said photoactivatable compound is an aryl azide group, and following the immune determination recovering the carrier material with the component bound thereon.

6. Process according to claim 5, wherein the photoactivatable compound is N-succinimidyl 6-(4'-azido-2'-nitrophenylamino)-hexanoate.

7. In a process for immune determination comprising the steps of covalently binding a heterobifunctional photoactivatable compound to protein A agglutinogen from *Staphylococcus aureus* to form a heterobifunctional photoactivatable compound - protein A complex, covalently binding said complex to a polyethylene carrier material, binding an antibody reaction component of an immune reaction with its constant part to the protein A, carrying out the immune determination and recovering the carrier material with the complex and antibody reaction compound bound thereon.

8. Process according to claim 7, wherein the binding of the antibody reaction component to the protein A is by covalent binding via a heterobifunctional photoactivatable compound.

9. Process according to claim 8, wherein the heterobifunctional photoactivatable compound is N-hydroxysuccinimidyl-4-azidosalicyclic acid or N-succinimidyl-6-(4'-azido-2'-nitrophenylamino)-hexanoate.

* * * * *